(12) United States Patent
Kling et al.

(10) Patent No.: US 11,717,533 B2
(45) Date of Patent: Aug. 8, 2023

(54) ZINC COMPOSITION AND THEIR USE IN ANTI-MICROBIAL APPLICATIONS

(75) Inventors: William O. Kling, Dallas, TX (US); Laura K. S. Parnell, Missouri City, TX (US)

(73) Assignee: Swiss-American CDMO LLC, Carrollton, TX (US)

( * ) Notice: Subject to any disclaimer, the term of this patent is extended or adjusted under 35 U.S.C. 154(b) by 614 days.

(21) Appl. No.: 11/644,396

(22) Filed: Dec. 21, 2006

(65) Prior Publication Data

US 2007/0190177 A1 Aug. 16, 2007

Related U.S. Application Data

(60) Provisional application No. 60/752,812, filed on Dec. 22, 2005.

(51) Int. Cl.
*A61K 33/30* (2006.01)
*A61K 31/315* (2006.01)
*A01N 59/16* (2006.01)
*A61K 31/555* (2006.01)
*A61K 45/06* (2006.01)
*A61K 31/355* (2006.01)

(52) U.S. Cl.
CPC .............. *A61K 33/30* (2013.01); *A01N 59/16* (2013.01); *A61K 31/315* (2013.01); *A61K 31/355* (2013.01); *A61K 31/555* (2013.01); *A61K 45/06* (2013.01)

(58) Field of Classification Search
CPC .... A61K 33/30; A61K 31/315; A61K 31/355; A61K 31/555; A61K 45/06; A01N 59/16
See application file for complete search history.

(56) References Cited

U.S. PATENT DOCUMENTS

| | | | | |
|---|---|---|---|---|
| 3,404,987 A * | 10/1968 | Kooistra | ................ | A01N 59/16 424/603 |
| 4,315,927 A * | 2/1982 | Evans | .................. | C07D 213/79 426/2 |
| 5,922,311 A * | 7/1999 | Terren | ...................... | A61K 8/06 424/59 |
| 6,290,940 B1 * | 9/2001 | Meyers et al. | .................. | 424/64 |
| 2003/0099745 A1 * | 5/2003 | Grinstead | ................ | A23B 4/20 426/335 |
| 2003/0152644 A1 * | 8/2003 | Modak et al. | ................ | 424/667 |
| 2004/0266852 A1 * | 12/2004 | Coleman | ................ | A01N 37/02 514/400 |
| 2005/0151117 A1 * | 7/2005 | Man | ....................... | A01N 37/16 252/186.1 |

FOREIGN PATENT DOCUMENTS

WO WO 03/066001 * 8/2003

OTHER PUBLICATIONS

Martin, W. Ann. Surg. 1922; 76(1): 13-27.*
Kabara et al. Antimicrobial Agents and Chemotherapy. 1972; 2(1): 23-28.*
Mokbel et al. Am J Biochem Biotech. 2005; 1(3): 125-131. (Year: 2005).*
Fuursted et al. J Antimicrobial Chemotherapy. 1997; 40: 221-226. (Year: 1997).*
Stickler et al. Eur J Clin Microbiol & Infect Dis. 1989; 8(11): abstract (Year: 1989).*
Conner et al. Appl Environ Microbiol. 1995; 61(1): 382-385. (Year: 1995).*

\* cited by examiner

*Primary Examiner* — David Browe
(74) *Attorney, Agent, or Firm* — Winstead PC

(57) ABSTRACT

The invention relates generally to antimicrobial compositions that are non-toxic to mammals and plants, and are highly effective against a broad spectrum of detrimental pathogenic microorganisms. The antimicrobial compositions contain at least one zinc compound that is microbicidal to at least one microorganism. The antimicrobial compositions of the invention can be diluted in suitable proportions into suitable solvents to produce the desired dosages for each individual application. The antimicrobial compositions can be applied by conventional methods, e.g., spraying, soaking, fogging, impregnation, and the like. The compositions can also be used as preservatives. The antimicrobial compositions can also be made as gels or solids in different forms by using techniques available to those skilled in the art.

6 Claims, No Drawings

ZINC COMPOSITION AND THEIR USE IN ANTI-MICROBIAL APPLICATIONS

CROSS REFERENCES TO RELATED APPLICATIONS

This application claims the benefit of U.S. Provisional Application No. 60/752,812, filed Dec. 22, 2005.

BACKGROUND OF THE INVENTION

1. Technical Field of the Invention

The invention relates generally to zinc compounds and their use in antimicrobial applications.

2. Description of the Prior Art

At a time when microbial resistance is a constant threat, the need for new antimicrobials is greater than ever. Topical antimicrobial hand-washes are used on intact skin by consumers for self-protection and by medical staff to protect themselves and patients from transferred microbes. Topical antimicrobials are also used on wounded skin to prevent bacteria from invading the wound. Once bacteria invade a wound, the detrimental effects can range from a delay in healing to death by sepsis.

Some heavy metals are known to exert antimicrobial effects. Silver-based dressings are currently used as wound dressings to reduce the microbial burden of the wound. Zinc is a metal that has been purported to have antimicrobial properties. Upon close review of the literature however, not all products containing zinc have been consistent at reducing the microbial burden or aiding in the healing of wounds. There are several articles in which safety, absorption, and activity of zinc have been called into question. Review of the published literature and prior art indicates that products capable of consistently producing an antimicrobial affect are either drugs such as sulfadiazine or pyrithione that are combined with zinc, or other antimicrobial compounds in combination with zinc. Use of these compositions can be problematic for two reasons. First, when drugs are used topically, the majority of them will cause an increase in bacterial resistance to the drug component. Secondly, many antimicrobial compounds can act as an irritant and can sensitize people. Upon application of the compound following sensitization, the reaction can range from raised whelps to anaphylactic shock, which in turn can lead to death.

Metals such as aluminum, barium, beryllium, bismuth, cadmium, calcium, chromium, cobalt, copper, gallium, germanium, gold, indium, iron, lead, magnesium, manganese, molybdenum, nickel, palladium, platinum, scandium, silver, strontium, tin, titanium, vanadium, and zinc have varying antimicrobial affects. Each element has advantages and disadvantages. Some are antimicrobial, but extremely toxic. Others have a good antimicrobial spectrum, but are expensive and/or rare. Calcium, chromium, copper, iron, magnesium, manganese, and zinc are all known to be used within the body and would be logical choices to include in testing.

Zinc has an excellent safety profile, does not cross the blood brain barrier, can be eliminated by the body, and poses little risk, thereby making zinc an agent of choice for reducing microbes in humans and animals. In addition, zinc is an essential nutrient that has been implicated in accelerating healing in elderly and zinc deficient people. There is therefore a need for antimicrobial compositions that can be used topically without resulting in adverse effects to user.

Specific applications contemplated by the present invention include the use of zinc compounds as disinfectants and preservatives, where the presence of zinc inhibits microbial growth.

There is also a need for a compound that can be used safely as a preservative without displaying any toxic effects, while maintaining its efficacy over time. Many preservatives work well, but require a low pH which may not be beneficial to the product end use. Preservatives such as sodium benzoate or potassium sorbate are not considered strong preservatives and can be neutralized by exposure to common ingredients and thus rendering the substance inactive and unprotected. Some foods and products are irradiated to prevent bacterial growth and increase the shelf life, but once the product is used, no protection is present. Items that are not single use items are particularly susceptible to microbial growth due to repeated exposure. For infants and elderly who have incompetent immune systems, low levels of microbial growth can cause sickness or death not seen in people with a healthy immune system. Common preservatives such as mercury, methylparabens, and azides act after the product is used, but have raised safety concerns. Zinc's safety profile makes it the ideal candidate for use as a preservative.

SUMMARY OF THE INVENTION

The invention relates to a method of controlling microbial growth by introducing an effective amount of an antimicrobial composition having an effective amount of a zinc compound.

The invention also relates to a composition for controlling microbial growth, where the composition contains an effective amount of a zinc compound.

DESCRIPTION OF ILLUSTRATIVE EMBODIMENTS

The inventive compositions described herein have consistently exhibited antimicrobial activity, which does not appear to be related to the coupling compounds that may be additionally present in the compositions. Because of these results, the antimicrobial activity can be attributed to the zinc itself.

As used herein, the term "antimicrobial composition" refers to a composition having the ability to effect at least a 90% reduction (1-log order reduction) in the population of bacteria and other microbes, and thereby control the growth of microorganisms. The control of the growth of microorganisms may also be referred to as antimicrobial activity. Also preferably, the antimicrobial compositions of the invention provide greater than a 99% reduction (2-log order reduction), more preferably greater than a 99.99% reduction (4-log order reduction), and most preferably greater than a 99.999% reduction (5-log order reduction) in the microbial population. Because in their broadest sense these definitions for antimicrobial activity are different from some of the current governmental regulations, the use in connection with this invention of the term "antimicrobial" is not intended to indicate compliance with any particular governmental standard for antimicrobial activity. The antimicrobial compositions of the invention include sterilants, sanitizers, disinfectants, and preservatives.

As used in this invention, the term "sterilant" refers to a physical or chemical agent or process capable of destroying all forms of life (including bacteria, viruses, fungi, and spores) on inanimate surfaces.

As used in this invention, the term "sanitizer" refers to an agent that reduces the number of bacterial contaminants to safe levels as judged by public health requirements. Preferably, sanitizers for use in this invention will provide at least a 99.999% reduction (5-log order reduction) in the microbial population.

As used in this invention, the term "disinfectant" refers to an agent that kills all vegetative cells including most recognized pathogenic microorganisms on soft or hard surfaces.

As used in this invention, the term "preservative" refers to an agent that extends the storage life of food and non-food products by retarding or preventing deterioration of flavor, odor, color, texture, appearance, nutritive value, or safety. A preservative need not provide a lethal, irreversible action resulting in partial or complete microbial cell destruction or incapacitation.

Sterilants, sanitizers, disinfectants, sporicides, viracides and tuberculocidal agents provide such an irreversible mode of action, sometimes referred to as "bactericidal" action. In contrast, a preservative can provide an inhibitory or bacteriostatic action that is reversible, in that the target microbes can resume multiplication if the preservative is removed. The principal differences between a preservative and a sanitizer primarily involve mode of action (a preservative prevents growth rather than aggressively killing microorganisms) and exposure time (a preservative has days to months to act whereas a sanitizer has at most a few minutes to act).

According to the present invention, controlling the growth of at least one microorganism, i.e., antimicrobial activity, includes both the reduction and/or prevention of such growth. It is to be further understood that by "controlling," the growth of at least one microorganism is inhibited. In other words, there is no growth or substantially no growth of at least one microorganism. "Controlling" the growth of at least one microorganism includes maintaining a microorganism population at a desired level (including undetectable levels such as zero population), reducing a microorganism population to a desired level, and/or inhibiting or slowing the growth of at least one microorganism. Thus, materials and mediums susceptible to attack by at least one microorganism are preserved and/or protected from this attack and the resultant deleterious effects. The present invention also provides a method for controlling the growth of at least one microorganism in or on a material or medium susceptible to attack by the microorganism which comprises the step of adding to the material or medium a composition of the present invention in an amount effective to control the growth of the microorganism.

The mode as well as the rates of distribution and application of the compositions of this invention could vary depending upon the intended use. The compositions could be applied by spraying or brushing onto a material or product. The material or product in question could also be treated by dipping in a suitable formulation of the composition. In a liquid or liquid-like medium, the composition could be added into the medium by pouring or by metering with a suitable device so that a solution or dispersion of the composition can be produced. Thus, the substrates or materials susceptible to attack by these types of microorganisms are preserved from this attack and the resulting spoilage or other detrimental effects caused by the microorganisms. Further, it is to be understood that "controlling" the growth of at least one microorganism also includes biostatically reducing and/or maintaining a low level of microorganisms such that the attack by microorganisms and any resulting spoilage or other detrimental effects are mitigated, i.e., the microorganism growth rate or microorganism attack rate is slowed down or eliminated.

Microorganisms, as used herein, include, but are not limited to bacteria, both gram-positive and gram-negative, fungi, algae, viruses, amoebae, spores, and the like, and include both yeast and molds.

The antimicrobial compositions of the invention described herein have a plethora of applications and uses. They are suitable for the sterilization of drinking water, suitable for the beverage and food industry, suitable for sterilizing exposed surfaces, exhaust air and ventilation components, animal feed, suitable for use in the pharmaceutical industry, in hospitals, for surgical equipment, in swimming pools, in saunas, and for fish, poultry, and cattle farming, and the like.

In an embodiment of the invention, a blend of zinc salts, colloidal zinc, zinc ligands, zinc alloys, or other zinc compounds with various dissociation rates are used to make the antimicrobial compositions. The varying dissociation rates are important for ensuring constant antimicrobial activity during the period of application of zinc-based composition.

In an embodiment of the invention, the zinc compounds used in the compositions of the invention are selected from the group consisting of zinc acetate, zinc butyrate, zinc chloride, zinc citrate, zinc gluconate, zinc glycerate, zinc glycolate, zinc formate, zinc lactate, zinc phthalocyanine, zinc picolinate, zinc proprionate, zinc salicylate, zinc tartrate and zinc undecylenate.

An exemplary composition of the invention is made up of at least 0.05 wt % of a first zinc compound in a suitable solvent that is capable of completely solubilizing the zinc compound.

In another embodiment of the invention, the concentration of the first zinc compound ranges from between 0.10 wt % to 25 wt %

In certain embodiments, the compositions of the invention comprise additional zinc compound(s). The concentration of the additional zinc compound can range from 0.01 wt % to 10 wt %.

In vitro studies have been performed to optimize and ascertain the antimicrobial activity of the invention. Contrary to anecdotal data found in the literature, formulations of the invention have been shown to exhibit antimicrobial activity against a variety of microbes including, but not limited to, bacteria, fungi, molds, yeast and viruses. In addition, the compositions of the invention are efficacious against other types of microbes including, but not limited to, algae and protozoa.

Tests have been performed in vivo and in vitro to determine the cytotoxic effects of the compositions of the invention. The tests indicate that the compositions of the claimed invention exhibit minimal levels of cytotoxicity and thus are suitable and safe for use in humans and animals.

When applied to microbes (e.g., when applied to a surface containing microbes), the compositions of the invention exhibit antimicrobial action. As shown in the Working Examples set out below, very rapid and substantially complete antimicrobial action can be attained.

The compositions of the invention can be used either directly, by introduction to a system, e.g., a foodstuff or material, or can be diluted with suitable solvents to provide the necessary antimicrobial activity, depending on the application.

The compositions of the invention can be formulated and sold for use as is, or as solvent concentrates. If desired, such concentrates can be used full-strength as antimicrobial agents.

A variety of fluids can be used as a carrier vehicle or diluting solvent, including water in its liquid and gaseous forms; as well as saline, lipid/oil, silicone, alcohol solvents. The compositions of the invention can be formulated to include the diluting solvent as sold, or the diluting solvent can be added at any time up to the time of use. A variety of dilution ratios can be employed, so long as the diluted composition exhibits the desired antimicrobial behavior when applied to the target microbes. The concentration of carrier vehicle can represent about 0.01 wt % to about 99.9 wt % of the diluted mixture, more preferably about 50 wt % to about 95 wt %, and most preferably about 75 wt % to about 25 wt %.

A variety of surfactants can be employed. In general, the surfactant identity and use level is selected based upon the characteristics of the chosen solvent. For compositions in which water serves as the diluting solvent, the surfactant preferably will have an HLB value greater than or equal to about 13, or less than or equal to about 6. Preferably, the surfactant does not tend to cause formation of insoluble deposits, and has low odor and low toxicity. Mixtures of surfactants can be used if desired.

Preferred anionic surfactants include C6-C24 alkylbenzene sulfonates; C6-C24 olefin sulfonates; C6-C24 paraffin sulfonates; cumene sulfonate; xylene sulfonate; C6-C24 alkyl naphthalene sulfonates; C6-C24 alkyl or dialkyl diphenyl ether sulfonates or disulfonates, C4-C24 mono or dialkyl sulfosuccinates; sulfonated or sulfated fatty acids; C6-C24 alcohol sulfates (preferably C6-C12 alcohol sulfates); C6-C24 alcohol ether sulfates having 1 to about 20 ethylene oxide groups; and C4-C24 alkyl, aryl or alkaryl phosphate esters or their alkoxylated analogues having 1 to about 40 ethylene, propylene or butylene oxide units or mixtures thereof.

Preferred nonionic surfactants include C6-C24 alcohol ethoxylates (preferably C6-C14 alcohol ethoxylates) having 1 to about 20 ethylene oxide groups (preferably about 9 to about 20 ethylene oxide groups); C6-C24 alkylphenol ethoxylates (preferably C8-C10 alkylphenol ethoxylates) having 1 to about 100 ethylene oxide groups (preferably about 12 to about 20 ethylene oxide groups); C6-C24 alkylpolyglycosides (preferably C6-C20 alkylpolyglycosides) having 1 to about 20 glycoside groups (preferably about 9 to about 20 glycoside groups); C6-C24 fatty acid ester ethoxylates, propoxylates or glycerides; and C4-C24 mono or di alkanolamides.

The antimicrobial compositions of the invention should not contain excessive amounts of surfactant since larger amounts of surfactant may diminish the antimicrobial effectiveness of the compositions of the invention. Instead, the amount of surfactant should be just sufficient to provide the desired level of antimicrobial activity. Usually, the solvent concentrates of the invention will contain no more than about 10 wt. % surfactant, more preferably 0 to about 3 wt % surfactant and most preferably 0 to about 1 wt. % surfactant. Most preferably, the concentrates are substantially surfactant-free.

The antimicrobial compositions of the invention may also contain an additional antimicrobial agent. This additional antimicrobial agent can be dissolved or dispersed in the antimicrobially-active solvent or in the diluting solvent. Desirably, the additional antimicrobial agent will preferentially dissolve or disperse in the antimicrobially-active solvent rather than in the diluting solvent. Suitable additional antimicrobial agents include carboxylic acids, diacids, or triacids (e.g., butyric acid, heptanoic acid, octanoic acid, nonanoic acid, decanoic acid, salycic acid, mandelic acid, succinic acid, adipic acid, glutaric acid, EDTA and citric acid), carboxylic esters (e.g., p-hydroxy alkyl benzoates and alkyl cinnamates), sulfonic acids (e.g., dodecylbenzene sulfonic acid), iodo-compounds or active halogen compounds (e.g., iodine, interhalides, polyhalides, metal hypochlorites, hypochlorous acid, metal hypbromites, hypobromous acid, chloro- and bromo-hydantoins, chlorine dioxide and sodium chlorite), active oxygen compounds including hydrogen peroxide, isolated or equilibrium derived or isolated peracids such as chloroperbenzoic acids, peracetic acid, perheptanoic acid, peroctanoic acid, perdecanoic acid, performic acid, percitric acid, perglycolic acid, perlactic acid, perbenzoic acid, and monoester peracids derived from diacids or diesters (e.g., such as adipic, succinic, glutaric, or malonic acid and mixtures thereof), organic peroxides including benzoyl peroxide, alkyl benzoyl peroxides, ozone, singlet oxygen generators, and mixtures thereof, phenolic derivatives (e.g., o-phenyl phenol, o-benzyl-p-chlorophenol, tert-amyl phenol and C1-C6 alkyl hydroxy benzoates), quaternary ammonium compounds (e.g., alkyldimethylbenzyl ammonium chloride, dialkyldimethyl ammonium chloride and mixtures thereof), and mixtures of such antimicrobial agents, in an amount sufficient to provide the desired degree of microbial protection.

If present in the antimicrobial compositions of the invention, the additional antimicrobial agent preferably is about 0.01 to about 30 wt. % of the concentrate, more preferably about 0.05 to about 10 wt. % and most preferably about 0.1 to about 5 wt. %.

It should be noted that the antimicrobial properties of certain embodiments of the invention are solely due to the one or more zinc compounds present in the compositions. Although secondary antimicrobial agents may be used in conjunction with the zinc compounds, they are not a required component of the compositions of the present invention. Thus, the antimicrobial properties of the compositions of the inventions are conferred primarily and, in certain cases, exclusively by the zinc compounds present in the invention.

In certain embodiments of the invention, the compositions of the present invention further comprise a silicone polymer. The concentration of the silicone polymer in the antimicrobial compositions can range from 0.1 wt % to 10 wt %. Examples of suitable silicone polymers include polydimethylsiloxane polymer, dimethiconol fluid in dimethicone, cyclomethicone, dimethicone copolyl, and silicone glycol.

Certain embodiments of the invention comprise one or more natural or synthetic chemicals. Examples of such chemicals include, monoterpene hydrocarbon, sesquiterpene hydrocarbon, monoterpene alcohol, sesquiterpene alcohol, monoterpene ester, sesquiterpene ester, monoterpene ether, sesquiterpene ether, monoterpene aldehyde, sesquiterpene aldehyde monoterpene ketone, sesquiterpene ketone, monoterpene oxide, sesquiterpene oxide, almond oil, ylang-ylang oil, neroli oil, sandalwood oil, frankincense oil, peppermint oil, lavender oil, jasmine absolute, geranium oil bourbon, spearmint oil, clove oil, lemongrass oil, cedarwood oil, balsam oils, tangerine oil, l-citronellol, a-amylcinnamaldehyde, lyral, geraniol, famesol, hydroxycitronellal, isoeugenol, eugenol, eucalyptus oil, eucalyptol, lemon oil, linoleic acid, linalool and citral.

Other embodiments of the inventions may contain effective amounts of one or more of chlorhexidine gluconate, benzalkonium chloride and incroquat.

If desired, the antimicrobial compositions of the invention can contain various adjuvants such as chelants, builders, thickeners, fragrances, dyes, pH adjusters, anticorrosion additives, antirust additives and indicators. The types and amounts of such adjuvants will be apparent to those skilled in the art.

Embodiments of the invention can provide antimicrobial compositions that display antimicrobial activity at any pH ranging from 1 to 13 depending on the compound(s) and amounts used. More specifically, the optimal pH range is 5.7-8.0 for contact with mammalian tissue depending on the compound(s) used and the end use. Inanimate objects may benefit from a wider acidic or basic pH range such as 2-11 dependent on the makeup of the object and the end use. The working examples of beverages, foodstuffs, medicines, cosmetics, and materials were tested with embodiments utilizing a pH range of 5.8-6.0. The antimicrobial composition of the invention is capable of exhibiting antimicrobial activity at all temperatures tested.

The compositions of the invention can be sold in the form of a kit containing the composition together with suitable directions for carrying out the method of the invention. Such directions typically will include recommended dilution ratios, applications, application techniques and safety warnings.

The antimicrobial compositions of the invention can be used for a variety of domestic or industrial applications, e.g., to reduce microbial or viral populations on a surface or object or on or in food or in a body or stream of water. The compositions can be applied in a variety of areas including kitchens, bathrooms, factories, hospitals, dental offices and food plants, and can be applied to a variety of hard or soft surfaces having smooth, irregular or porous topography. Suitable hard surfaces include, for example, architectural surfaces (e.g., floors, walls, windows, sinks, tables, counters and signs); eating utensils; hard-surface medical or surgical instruments and devices; and hard-surface packaging. Such hard surfaces can be made from a variety of materials comprising, for example, ceramic, metal, glass, wood or hard plastic. Suitable soft surfaces include, for example paper; filter media, hospital and surgical linens and garments, or mattress covers; soft-surface medical or surgical instruments and devices; and soft-surface packaging. Such soft surfaces can be made from a variety of materials comprising, for example, paper, fiber, woven or nonwoven fabric, soft plastics and elastomers. The compositions of the invention can also be applied to soft surfaces such as food and skin. The compositions are also suitable for application to growing or harvested plant material including leaves, stems, tubers, roots, seeds, and the like. One benefit of the invention is specific forms do not degrade soft plastics and elastomers like many corrosive containing germicides (e.g. chlorides).

The antimicrobial compositions of the invention can be included in products such as sterilants, sanitizers, disinfectants, preservatives, deodorizers, antiseptics, fungicides, germicides, sporicides, virucides, detergents, bleaches, hard surface cleaners, hand soaps and pre- or post-surgical scrubs. The compositions have particular utility as cold or hot aseptic packaging treatments. The antimicrobial compositions can also be used in veterinary products such as mammalian skin treatments or in products for sanitizing or disinfecting animal enclosures, pens, watering stations, and veterinary treatment areas such as inspection tables and operation rooms.

Safety profile of the compositions of the present invention is good for food. The antimicrobial compositions can also be used on foods and plant species to reduce surface microbial populations; used at manufacturing or processing sites handling such foods and plant species; or used to treat process waters around such sites. For example, the compositions can be used on food transport lines (e.g., as belt sprays); boot and hand-wash dip-pans; food storage facilities; anti-spoilage air circulation systems; refrigeration and cooler equipment; beverage chillers and warmers, blanchers, cutting boards, third sink areas, and meat chillers or scalding devices. The compositions of the invention can be used to treat produce transport waters such as those found in flumes, pipe transports, cutters, slicers, blanchers, retort systems, washers, and the like.

The antimicrobial compositions have particular value for use on food packaging materials and equipment, and especially for cold or hot aseptic packaging. The compositions can also be used on or in ware wash machines, dishware, bottle washers, bottle chillers, warmers, third sink washers, cutting areas (e.g., water knives, slicers, cutters and saws) and egg washers. Particular foodstuffs that can be treated with compositions of the invention include eggs, meats, seeds, leaves, fruits and vegetables. Particular plant surfaces include both harvested and growing leaves, roots, seeds, skins or shells, stems, stalks, tubers, corms, fruit, and the like. Particular treatable surfaces include packaging such as cartons, bottles, films and resins; dish ware such as glasses, plates, utensils, pots and pans; ware wash machines; exposed food preparation area surfaces such as sinks, counters, tables, floors and walls; processing equipment such as tanks, vats, lines, pumps and hoses (e.g., dairy processing equipment for processing milk, cheese, ice cream and other dairy products); and transportation vehicles.

The antimicrobial compositions can also be used on or in other industrial equipment and in other industrial process streams such as heaters, cooling towers, boilers, retort waters, rinse waters, aseptic packaging wash waters, and the like. The compositions can be used to treat microbes and odors in recreational waters such as in pools, spas, recreational flumes and water slides, fountains, and the like.

The antimicrobial compositions can also be used to reduce microbial and viral counts in air and liquids by incorporation into filtering media or breathing filters, e.g., to remove water and air-born pathogens such as *Legionella.*

Other hard surface cleaning applications for the antimicrobial compositions of the invention include clean-in-place systems (CIP), clean-out-of-place systems (COP), washer-decontaminators, sterilizers, textile laundry machines, ultra and nano-filtration systems and indoor air filters. COP systems can include readily accessible systems including wash tanks, soaking vessels, mop buckets, holding tanks, scrub sinks, vehicle parts washers, non-continuous batch washers and systems, and the like. CIP systems include a variety of devices that will be familiar to those skilled in the art, and will typically employ flow rates on the order of about 40 to about 600 liters per minute, temperatures from ambient up to about 70° C., and contact times of at least about 10 seconds, more preferably about 30 to about 120 seconds.

The antimicrobial compositions can be introduced into an article or product or onto a surface, either a soiled surface containing microbes, or a cleaned surface, using a variety of methods such as spraying, soaking, fogging, and impregnation. For example, the antimicrobial composition can be sprayed or wiped onto a surface; the composition can be caused to flow over the surface, or the surface can be dipped into the composition. Additionally, the composition can be incorporated into the product, particularly food and beverage products, or products such as make-up and cosmetics, during the manufacture of the product. In these instances, the antimicrobial composition is uniformly integrated with the remainder of the product. The compositions of the invention can be formulated as liquids, gels, aerosols, waxes, solids, or powders. If steam or another gaseous diluting solvent is employed, then the compositions can be formulated to be applied in a gaseous state.

The present invention is also effective in controlling biological fouling. biological fouling (biofouling) is the undesirable accumulation of microorganisms, plants and animals on artificial surfaces. This occurs on artificial surfaces submerged in seawater (marine biofouling), such as ship's hulls, seaside piers and sea defenses, as well as on other surfaces that are in continuous contact with water, such as air conditioning systems and water pipes.

The antimicrobial compositions of the invention can be introduced directly into the source of where the biofouling is occurring or can be mixed with appropriate solvents and introduced into the area where biofouling is occurring.

Another beneficial use of the present invention is with respect to preserving or extending the life of flowers and plants. The present invention can be used as a preservative for cut flowers and cut plants by including the formulation of the present invention in the water in which the cut flowers or plants are placed into or can be formulated into a powder or tablet which can be introduced into the container holding the cut flowers or plants. Also, the formulations of the present invention can be used as a spray which is applied to living plants and flowers and acts as an agent to control pests, insects, and/or microorganisms and thus preserves a living plant and protects the plant from plant diseases, bacteria, viruses, fungus, algae, insects, and the like. The amount of the formulation which is used depends upon the plant or flowers and as described above, is typically a diluted composition containing the antimicrobial compositions of the present invention.

The present invention is further illustrated by the following non-limiting examples. These experiments constitute some of the embodiments of the invention herein disclosed.

WORKING EXAMPLES

Several compositions of the invention were tested for their ability to display antimicrobial properties. The compositions used in the examples below contained one or more zinc compounds at a concentration ranging from 0.05 wt % to 25 wt % in a suitable solvent, and did not contain any other compound or agent having known antimicrobial properties. The working pH in all of the examples ranged from 5.8-6.0.

Test Organisms:

Cultures of the following microorganisms are maintained as stock cultures from which working inocula are prepared. The viable microorganisms used in this test must not be more than five passages removed from the original stock culture. For purposes of the test, one passage is defined as the transfer of organisms from an established culture to fresh medium.

A. *E. coli* (ATCC No. 8739, Quality Technologies, Inc.)
B. *S. aureus* (ATCC No. 6538, Quality Technologies, Inc.)
C. *P. aeruginosa* (ATCC No. 9027, Quality Technologies, Inc.)
D. *C. albicans* (ATCC No. 10231, Quality Technologies, Inc.)
E. *A. niger* (ATCC No. 16404, Quality Technologies, Inc.)

Preservative Challenge Test Procedure:

Inoculate the surface of a suitable volume of solid agar medium from a recently grown stock culture of each of the specified microorganisms. Incubate the bacterial and fungal cultures at 35° C.+/−2° C. for 24-48 hours. Incubate the fungal cultures at 25° C.+/−2° C. for an additional 2-4 days. Determine the number of viable microorganisms in each milliliter of the inoculum suspensions by serial dilution in sterile phosphate buffered saline. Plate dilutions of 10-6 and 10-8 for the test organisms. Overlay with approximately 20 ml of 45° C. Tryptic Soy Agar with lecithin and Tween 80. Incubate for 24-48 hours at 35° C.+/−2° C. for the aerobic organisms. Incubate for an additional 2-4 days at 25° C.+/−2° C. for the fungal organisms. Count test organisms and calculate number of organisms as colony forming units.

Beverages: The mouth contains high levels of microbes. Once a drink is taken from a beverage, regardless if from the rim of the container or from a straw, the beverage is contaminated with microbes. The microbes typically will begin proliferating almost immediately resulting in a contaminated beverage, which may or may not taste or smell different. Presence of at least one composition of the invention in the food and/or beverage showed a greater than 99.999% reduction (5-log order reduction) in a microbial load using a modified preservative challenge test. See Table 1. The preservative efficacy test demonstrated the zinc treated infant formula and Gatorade Passed the test for all five organisms tested against. The preservative efficacy test demonstrated the untreated infant formula and Gatorade Failed the test for all five organisms tested against.

TABLE 1

| Organisms | Similac Advanced Infant Formula Not Treated | | Similac Advanced Infant Formula Zinc Treated | | Lemon Lime Gatorade Not Treated | | Lemon Lime Gatorade Zinc Treated | |
|---|---|---|---|---|---|---|---|---|
| | Average CFU | Log Reduction | Average CFU | Log Reduction | Average CFU | Log Reduction | Average CFU | Log Reduction |
| *E. coli* 0 hours | $6.57 \times 10^5$ | 0 | $6.57 \times 10^5$ | 0 | $6.57 \times 10^5$ | 0 | $6.57 \times 10^5$ | 0 |
| *E. coli* 8 hours | $2.20 \times 10^6$ | −0.52 | 460 | 3.15 | $3.30 \times 10^5$ | 0.34 | 45 | 4.16 |
| *E. coli* 24 hours | $7.90 \times 10^7$ | −2.08 | No Growth | 5.82 | $6.00 \times 10^6$ | −0.96 | No Growth | 5.82 |
| *E. coli* 7 days | 2,080 | 2.50 | No Growth | 5.82 | 2,912 | 2.35 | No Growth | 5.82 |

TABLE 1-continued

| Organisms | Similac Advanced Infant Formula Not Treated | | Similac Advanced Infant Formula Zinc Treated | | Lemon Lime Gatorade Not Treated | | Lemon Lime Gatorade Zinc Treated | |
|---|---|---|---|---|---|---|---|---|
| | Average CFU | Log Reduction | Average CFU | Log Reduction | Average CFU | Log Reduction | Average CFU | Log Reduction |
| E. coli 14 days | $5.2 \times 10^6$ | −0.90 | No Growth | 5.82 | $2.91 \times 10^6$ | −0.65 | No Growth | 5.82 |
| E. coli 21 days | TNTC | TNTC | No Growth | 5.82 | $1.50 \times 10^6$ | −0.36 | No Growth | 5.82 |
| E. coli 28 days | TNTC | TNTC | No Growth | 5.82 | $3.22 \times 10^6$ | −0.69 | No Growth | 5.82 |
| S. aureus 0 hours | $7.07 \times 10^5$ | 0 | $7.07 \times 10^5$ | 0 | $7.07 \times 10^5$ | 0 | $7.07 \times 10^5$ | 0 |
| S. aureus 8 hours | $2.00 \times 10^6$ | −0.45 | 1,513 | 2.67 | $5.21 \times 10^5$ | 0.13 | 125 | 3.75 |
| S. aureus 24 hours | $4.85 \times 10^6$ | −0.84 | No Growth | 5.85 | $8.00 \times 10^5$ | −0.05 | No Growth | 5.85 |
| S. aureus 7 days | 1,924 | 2.57 | No Growth | 5.85 | 2.184 | 2.51 | No Growth | 5.85 |
| S. aureus 14 days | $3.95 \times 10^6$ | −0.75 | No Growth | 5.85 | $2.81 \times 10^6$ | −0.60 | No Growth | 5.85 |
| S. aureus 21 days | TNTC | TNTC | No Growth | 5.85 | $3.00 \times 10^6$ | −0.63 | No Growth | 5.85 |
| S. aureus 28 days | TNTC | TNTC | No Growth | 5.85 | $2.60 \times 10^6$ | −0.57 | No Growth | 5.85 |
| P. aeruginosa 0 hours | $1.52 \times 10^5$ | 0 | $1.52 \times 10^5$ | 0 | $1.52 \times 10^5$ | 0 | $1.52 \times 10^5$ | 0 |
| P. aeruginosa 8 hours | $7.00 \times 10^5$ | −0.66 | 120 | 3.10 | $1.00 \times 10^6$ | −0.82 | No Growth | 5.18 |
| P. aeruginosa 24 hours | $4.24 \times 10^7$ | −2.44 | No Growth | 5.18 | $4.35 \times 10^6$ | −1.46 | No Growth | 5.18 |
| P. aeruginosa 7 days | 2,080 | 1.86 | No Growth | 5.18 | 2,548 | 1.78 | No Growth | 5.18 |
| P. aeruginosa 14 days | $5.20 \times 10^6$ | −1.53 | No Growth | 5.18 | $2.80 \times 10^6$ | −1.27 | No Growth | 5.18 |
| P. aeruginosa 21 days | TNTC | TNTC | No Growth | 5.18 | $3.00 \times 10^6$ | −1.30 | No Growth | 5.18 |
| P. aeruginosa 28 days | TNTC | TNTC | No Growth | 5.18 | $4.06 \times 10^6$ | −1.43 | No Growth | 5.18 |
| C. albicans 0 hours | $2.70 \times 10^6$ | 0 | $2.70 \times 10^6$ | 0 | $2.70 \times 10^6$ | 0 | $2.70 \times 10^6$ | 0 |
| C. albicans 8 hours | $2.10 \times 10^6$ | 0.11 | $3.15 \times 10^6$ | −0.07 | $1.55 \times 10^6$ | 0.24 | $2.05 \times 10^6$ | 0.12 |
| C. albicans 24 hours | $1.55 \times 10^6$ | 0.24 | $2.20 \times 10^6$ | 0.09 | $3.05 \times 10^6$ | −0.05 | $1.50 \times 10^6$ | 0.26 |
| C. albicans 7 days | 1,612 | 3.22 | 2,340 | 3.06 | 1,820 | 3.17 | 2,652 | 3.01 |
| C. albicans 14 days | $3.48 \times 10^6$ | −0.11 | 298 | 3.96 | $3.48 \times 10^6$ | −0.11 | 200 | 4.13 |
| C. albicans 21 days | TNTC | TNTC | 900 | 3.48 | $1.00 \times 10^7$ | −0.57 | No Growth | 6.43 |
| C. albicans 28 days | TNTC | TNTC | 180 | 4.18 | $2.76 \times 10^6$ | −0.01 | No Growth | 6.43 |
| A. niger 0 hours | $5.91 \times 10^5$ | 0 | $5.91 \times 10^5$ | 0 | $5.91 \times 10^5$ | 0 | $5.91 \times 10^5$ | 0 |
| A. niger 8 hours | $4.50 \times 10^5$ | 0.12 | $5.50 \times 10^5$ | 0.03 | $4.00 \times 10^5$ | 0.17 | $5.00 \times 10^5$ | 0.07 |
| A. niger 24 hours | $3.50 \times 10^5$ | 0.23 | $5.50 \times 10^5$ | 0.03 | $1.10 \times 10^4$ | 1.73 | $7.50 \times 10^5$ | −0.10 |
| A. niger 7 days | 1,820 | 2.51 | 2,080 | 2.45 | 2,548 | 2.37 | No Growth | 5.77 |
| A. niger 14 days | $2.65 \times 10^6$ | −0.65 | $2.40 \times 10^4$ | 1.39 | $1.51 \times 10^6$ | −0.41 | No Growth | 5.77 |
| A. niger 21 days | TNTC | TNTC | 8,800 | 1.83 | $7.10 \times 10^4$ | 0.92 | No Growth | 5.77 |
| A. niger 28 days | TNTC | TNTC | 6,000 | 1.99 | $1.61 \times 10^6$ | −0.44 | No Growth | 5.77 |

*TNTC means Too Numerous To Count

Food Stuffs: The mouth contains high microbial levels. Once a food is bitten into or an eating utensil enters the mouth, the food is contaminated with microbes. Likewise, containers that are repeatedly opened, and small portions removed, and the whole container stored again, have an increased risk of microbial contamination. Microbes typically will begin proliferating almost immediately resulting in contaminated food stuffs, which may or may not taste or smell different. Presence of compositions of the invention showed a greater than 99.999% reduction (5-log order reduction) in a microbial load using a modified preservative challenge test. See Table 2 and Table 3. The preservative efficacy test demonstrated the zinc treated pudding, bread, and jelly Passed the test for all five organisms tested against. The preservative efficacy test demonstrated the untreated pudding and bread Failed the test for all five organisms tested against.

TABLE 2

| Organisms | Kraft Handi Snack Pudding Not Treated | | Kraft Handi Snack Pudding Zinc Treated | | 2 × 2 White Bread Squares Not Treated | | 2 × 2 White Bread Squares Zinc Treated | |
|---|---|---|---|---|---|---|---|---|
| | Average CFU | Log Reduction | Average CFU | Log Reduction | Average CFU | Log Reduction | Average CFU | Log Reduction |
| *E. coli* 0 hours | $2.02 \times 10^5$ | 0 | $2.02 \times 10^5$ | 0 | $2.02 \times 10^5$ | 0 | $2.02 \times 10^5$ | 0 |
| *E. coli* 8 hours | $4.87 \times 10^7$ | −2.38 | 3,430 | 1.77 | $8.00 \times 10^6$ | −1.60 | 1,258 | 2.21 |
| *E. coli* 24 hours | $5.70 \times 10^6$ | −1.45 | 2,760 | 1.86 | $1.20 \times 10^8$ | −2.77 | 180 | 3.05 |
| *E. coli* 7 days | $4.16 \times 10^6$ | −1.31 | No Growth | 5.31 | $5.51 \times 10^6$ | −1.44 | No Growth | 5.31 |
| *E. coli* 14 days | $2.03 \times 10^7$ | −2.00 | No Growth | 5.31 | $6.76 \times 10^7$ | −2.53 | No Growth | 5.31 |
| *E. coli* 21 days | $2.50 \times 10^7$ | −2.09 | No Growth | 5.31 | TNTC | TNTC | No Growth | 5.31 |
| *E. coli* 28 days | $4.68 \times 10^5$ | −0.37 | No Growth | 5.31 | $1.98 \times 10^7$ | −1.99 | No Growth | 5.31 |
| *S. aureus* 0 hours | $7.07 \times 10^5$ | 0 | $7.07 \times 10^5$ | 0 | $7.07 \times 10^5$ | 0 | $7.07 \times 10^5$ | 0 |
| *S. aureus* 8 hours | $5.85 \times 10^7$ | −1.92 | 5,000 | 2.15 | $2.90 \times 10^6$ | −0.61 | No Growth | 5.85 |
| *S. aureus* 24 hours | $9.85 \times 10^6$ | −1.14 | 2,753 | 2.41 | $4.33 \times 10^7$ | −1.79 | No Growth | 5.85 |
| *S. aureus* 7 days | $4.16 \times 10^6$ | −0.77 | No Growth | 5.85 | $3.64 \times 10^6$ | −0.71 | No Growth | 5.85 |
| *S. aureus* 14 days | $1.61 \times 10^7$ | −1.36 | No Growth | 5.85 | $4.47 \times 10^7$ | −1.80 | No Growth | 5.85 |
| *S. aureus* 21 days | $2.00 \times 10^7$ | −1.45 | No Growth | 5.85 | TNTC | TNTC | No Growth | 5.85 |
| *S. aureus* 28 days | $2.50 \times 10^7$ | −1.55 | No Growth | 5.85 | $1.00 \times 10^5$ | 0.85 | No Growth | 5.85 |
| *P. aeruginosa* 0 hours | $2.02 \times 10^5$ | 0 | $2.02 \times 10^5$ | 0 | $2.02 \times 10^5$ | 0 | $2.02 \times 10^5$ | 0 |
| *P. aeruginosa* 8 hours | $9.50 \times 10^6$ | −1.67 | 5,190 | 1.59 | $2.30 \times 10^5$ | −0.06 | No Growth | 5.31 |
| *P. aeruginosa* 24 hours | $3.48 \times 10^7$ | −2.24 | 2,618 | 1.89 | $3.74 \times 10^8$ | −3.27 | No Growth | 5.31 |
| *P. aeruginosa* 7 days | $3.90 \times 10^6$ | −1.29 | No Growth | 5.31 | $2.76 \times 10^6$ | −1.14 | No Growth | 5.31 |
| *P. aeruginosa* 14 days | $1.14 \times 10^7$ | −1.75 | No Growth | 5.31 | $3.07 \times 10^7$ | −2.18 | No Growth | 5.31 |
| *P. aeruginosa* 21 days | $3.00 \times 10^7$ | −2.17 | No Growth | 5.31 | TNTC | TNTC | No Growth | 5.31 |
| *P. aeruginosa* 28 days | $1.61 \times 10^7$ | −1.90 | No Growth | 5.31 | $2.40 \times 10^7$ | −2.08 | No Growth | 5.31 |
| *C. albicans* 0 hours | $1.92 \times 10^6$ | 0 | $1.92 \times 10^6$ | 0 | $1.92 \times 10^6$ | 0 | $1.92 \times 10^6$ | 0 |
| *C. albicans* 8 hours | $8.25 \times 10^6$ | −0.63 | $1.60 \times 10^6$ | 0.08 | $3.45 \times 10^6$ | −0.25 | $1.65 \times 10^6$ | 0.07 |
| *C. albicans* 24 hours | $3.39 \times 10^7$ | −1.25 | $1.60 \times 10^6$ | 0.08 | $1.96 \times 10^7$ | −1.01 | $1.35 \times 10^6$ | 0.15 |
| *C. albicans* 7 days | $5.88 \times 10^6$ | −0.49 | 500 | 3.58 | $3.12 \times 10^6$ | −0.21 | 510 | 3.58 |
| *C. albicans* 14 days | $3.43 \times 10^7$ | −1.25 | 140 | 4.14 | $2.44 \times 10^7$ | −1.10 | 30 | 4.81 |
| *C. albicans* 21 days | $2.50 \times 10^7$ | −1.12 | No Growth | 6.28 | TNTC | TNTC | No Growth | 6.28 |
| *C. albicans* 28 days | $3.10 \times 10^5$ | 0.79 | No Growth | 6.28 | $9.00 \times 10^4$ | 1.33 | No Growth | 6.28 |
| *A. niger* 0 hours | $3.76 \times 10^5$ | 0 | $3.76 \times 10^5$ | 0 | $3.76 \times 10^5$ | 0 | $3.76 \times 10^5$ | 0 |
| *A. niger* 8 hours | $3.50 \times 10^5$ | 0.03 | $4.50 \times 10^5$ | −0.08 | $4.50 \times 10^5$ | −0.08 | $2.50 \times 10^5$ | 0.18 |

TABLE 2-continued

| Organisms | Kraft Handi Snack Pudding Not Treated | | Kraft Handi Snack Pudding Zinc Treated | | 2 × 2 White Bread Squares Not Treated | | 2 × 2 White Bread Squares Zinc Treated | |
|---|---|---|---|---|---|---|---|---|
| | Average CFU | Log Reduction | Average CFU | Log Reduction | Average CFU | Log Reduction | Average CFU | Log Reduction |
| A. niger 24 hours | $5.40 \times 10^7$ | -2.16 | $4.50 \times 10^5$ | -0.08 | $8.05 \times 10^6$ | -1.33 | $3.00 \times 10^5$ | 0.10 |
| A. niger 7 days | $4.16 \times 10^6$ | -1.04 | 4,000 | 1.97 | $8.40 \times 10^4$ | 0.65 | No Growth | 5.58 |
| A. niger 14 days | $2.50 \times 10^7$ | -1.82 | 370 | 3.01 | $1.10 \times 10^6$ | -0.47 | No Growth | 5.58 |
| A. niger 21 days | $1.00 \times 10^4$ | 1.58 | No Growth | 5.58 | $1.20 \times 10^4$ | 1.50 | No Growth | 5.58 |
| A. niger 28 days | 20 | 4.27 | No Growth | 5.58 | $1.20 \times 10^4$ | 1.50 | No Growth | 5.58 |

TNTC means Too Numerous To Count

TABLE 3

| Organisms | Smucker's Grape Jelly Not Treated | | Smucker's Grape Jelly Zinc Treated | |
|---|---|---|---|---|
| | Average CFU | Log Reduction | Average CFU | Log Reduction |
| E. coli 0 hours | $6.57 \times 10^5$ | 0 | $6.57 \times 10^5$ | 0 |
| E. coli 8 hours | $3.50 \times 10^5$ | 0.27 | 45 | 4.16 |
| E. coli 24 hours | $2.49 \times 10^5$ | 0.42 | No Growth | 5.82 |
| E. coli 7 days | 2,236 | 2.47 | No Growth | 5.82 |
| E. coli 14 days | 130 | 3.70 | No Growth | 5.82 |
| E. coli 21 days | No Growth | 5.82 | No Growth | 5.82 |
| E. coli 28 days | No Growth | 5.82 | No Growth | 5.82 |
| S. aureus 0 hours | $7.07 \times 10^5$ | 0 | $7.07 \times 10^5$ | 0 |
| S. aureus 8 hours | $2.68 \times 10^5$ | 0.42 | No Growth | 5.85 |
| S. aureus 24 hours | $8.93 \times 10^4$ | 0.42 | No Growth | 5.85 |
| S. aureus 7 days | 1,456 | 2.69 | No Growth | 5.85 |
| S. aureus 14 days | $4.85 \times 10^5$ | 0.16 | No Growth | 5.85 |
| S. aureus 21 days | No Growth | 5.85 | No Growth | 5.85 |
| S. aureus 28 days | No Growth | 5.85 | No Growth | 5.85 |
| P. aeruginosa 0 hours | $1.52 \times 10^5$ | 0 | $1.52 \times 10^5$ | 0 |
| P. aeruginosa 8 hours | 880 | 2.23 | 5 | 4.48 |
| P. aeruginosa 24 hours | No Growth | 5.18 | No Growth | 5.18 |
| P. aeruginosa 7 days | No Growth | 5.18 | No Growth | 5.18 |
| P. aeruginosa 14 days | No Growth | 5.18 | No Growth | 5.18 |
| P. aeruginosa 21 days | No Growth | 5.18 | No Growth | 5.18 |
| P. aeruginosa 28 days | No Growth | 5.18 | No Growth | 5.18 |
| C. albicans 0 hours | $2.70 \times 10^6$ | 0 | $2.70 \times 10^6$ | 0 |
| C. albicans 8 hours | $2.25 \times 10^6$ | 0.08 | $1.35 \times 10^6$ | 0.30 |
| C. albicans 24 hours | $2.55 \times 10^6$ | 0.02 | $9.50 \times 10^5$ | 0.45 |
| C. albicans 7 days | 2,028 | 3.12 | 2,288 | 3.07 |
| C. albicans 14 days | $1.56 \times 10^6$ | 0.24 | 1,100 | 3.39 |
| C. albicans 21 days | $4.60 \times 10^5$ | 0.77 | No Growth | 6.43 |
| C. albicans 28 days | $3.38 \times 10^4$ | 1.90 | No Growth | 6.43 |
| A. niger 0 hours | $5.91 \times 10^5$ | 0 | $5.91 \times 10^5$ | 0 |
| A. niger 8 hours | $2.32 \times 10^5$ | 0.41 | $4.50 \times 10^5$ | 0.12 |
| A. niger 24 hours | $5.50 \times 10^5$ | 0.03 | $5.50 \times 10^5$ | 0.03 |
| A. niger 7 days | 68 | 3.94 | 1,768 | 2.52 |
| A. niger 14 days | $2.50 \times 10^5$ | 0.37 | $7.80 \times 10^4$ | 0.88 |
| A. niger 21 days | $2.00 \times 10^5$ | 0.47 | 8,100 | 1.86 |
| A. niger 28 days | $9.20 \times 10^6$ | -1.19 | 5,000 | 2.07 |

Medicinal and Cosmetic Products: Medicines, cosmetics, and other products are often opened repeatedly and used over time. For example, a jar of make-up or lotion is consumed over a period of weeks or even months. Repetitive exposure to microbes increases the risk of microbial contamination of the product by the user or by airborne microbes. Because many medicines and cosmetics are used on body areas more susceptible to microbes, preservatives with potential harmful side effects are often employed such as mercury or formaldehyde. Microbes typically will begin proliferating almost immediately unless inhibited by the preservatives resulting in a contaminated product, which may or may not look or smell different. Presence of compositions of the invention showed a greater than 99.999% reduction (5-log order reduction) in a microbial load using a modified preservative challenge test. See Table 4. The preservative efficacy test demonstrated the zinc treated contact solution and Day Quil Passed the test for all five organisms tested against. The preservative efficacy test demonstrated the untreated contact solution and Day Quil Passed the test for all five organisms tested against.

TABLE 4

| Organisms | B&L Sensitive Eyes Contact Lens Cleansing Saline Not Treated | | B&L Sensitive Eyes Contact Lens Cleansing Saline Zinc Treated | | Vicks Day Quil Not Treated | | Vicks Day Quil Zinc Treated | |
|---|---|---|---|---|---|---|---|---|
| | Average CFU | Log Reduction | Average CFU | Log Reduction | Average CFU | Log Reduction | Average CFU | Log Reduction |
| E. coli 0 hours | $6.57 \times 10^5$ | 0 | $6.57 \times 10^5$ | 0 | $6.57 \times 10^5$ | 0 | $6.57 \times 10^5$ | 0 |
| E. coli 8 hours | $1.02 \times 10^5$ | 0.81 | 105 | 3.80 | No Growth | 5.82 | No Growth | 5.82 |
| E. coli 24 hours | $2.70 \times 10^5$ | 1.39 | No Growth | 5.82 | No Growth | 5.82 | No Growth | 5.82 |
| E. coli 7 days | 484 | 3.13 | No Growth | 5.82 | No Growth | 5.82 | No Growth | 5.82 |
| E. coli 14 days | 26 | 4.40 | No Growth | 5.82 | No Growth | 5.82 | No Growth | 5.82 |
| E. coli 21 days | No Growth | 5.82 | No Growth | 5.82 | No Growth | 5.82 | No Growth | 5.82 |
| E. coli 28 days | No Growth | 5.82 | No Growth | 5.82 | No Growth | 5.82 | No Growth | 5.82 |
| S. aureus 0 hours | $7.07 \times 10^5$ | 0 | $7.07 \times 10^5$ | 0 | $7.07 \times 10^5$ | 0 | $7.07 \times 10^5$ | 0 |
| S. aureus 8 hours | $7.00 \times 10^5$ | 0.004 | No Growth | 5.85 | No Growth | 5.85 | No Growth | 5.85 |
| S. aureus 24 hours | $1.09 \times 10^5$ | 0.81 | No Growth | 5.85 | No Growth | 5.85 | No Growth | 5.85 |
| S. aureus 7 days | 172 | 3.61 | No Growth | 5.85 | No Growth | 5.85 | No Growth | 5.85 |
| S. aureus 14 days | 63 | 4.05 | No Growth | 5.85 | No Growth | 5.85 | No Growth | 5.85 |
| S. aureus 21 days | No Growth | 5.85 | No Growth | 5.85 | No Growth | 5.85 | No Growth | 5.85 |
| S. aureus 28 days | No Growth | 5.85 | No Growth | 5.85 | No Growth | 5.85 | No Growth | 5.85 |
| P. aeruginosa 0 hours | $1.52 \times 10^5$ | 0 | $1.52 \times 10^5$ | 0 | $1.52 \times 10^5$ | 0 | $1.52 \times 10^5$ | 0 |
| P. aeruginosa 8 hours | $2.70 \times 10^4$ | 0.75 | No Growth | 5.18 | No Growth | 5.18 | No Growth | 5.18 |
| P. aeruginosa 24 hours | 400 | 2.58 | No Growth | 5.18 | No Growth | 5.18 | No Growth | 5.18 |
| P. aeruginosa 7 days | No Growth | 5.18 | No Growth | 5.18 | No Growth | 5.18 | No Growth | 5.18 |
| P. aeruginosa 14 days | No Growth | 5.18 | No Growth | 5.18 | No Growth | 5.18 | No Growth | 5.18 |
| P. aeruginosa 21 days | No Growth | 5.18 | No Growth | 5.18 | No Growth | 5.18 | No Growth | 5.18 |
| P. aeruginosa 28 days | No Growth | 5.18 | No Growth | 5.18 | No Growth | 5.18 | No Growth | 5.18 |
| C. albicans 0 hours | $2.70 \times 10^6$ | 0 | $2.70 \times 10^6$ | 0 | $2.70 \times 10^6$ | 0 | $2.70 \times 10^6$ | 0 |
| C. albicans 8 hours | $2.55 \times 10^6$ | 0.02 | $1.40 \times 10^6$ | 0.29 | No Growth | 6.43 | No Growth | 6.43 |
| C. albicans 24 hours | $1.70 \times 10^6$ | 0.20 | $2.10 \times 10^6$ | 0.11 | No Growth | 6.43 | No Growth | 6.43 |
| C. albicans 7 days | 3,120 | 2.94 | No Growth | 6.43 | No Growth | 6.43 | No Growth | 6.43 |
| C. albicans 14 days | 377 | 3.86 | No Growth | 6.43 | No Growth | 6.43 | No Growth | 6.43 |
| C. albicans 21 days | 600 | 3.65 | No Growth | 6.43 | No Growth | 6.43 | No Growth | 6.43 |
| C. albicans 28 days | 440 | 3.79 | No Growth | 6.43 | No Growth | 6.43 | No Growth | 6.43 |
| A. niger 0 hours | $5.91 \times 10^5$ | 0 | $5.91 \times 10^5$ | 0 | $5.91 \times 10^5$ | 0 | $5.91 \times 10^5$ | 0 |
| A. niger 8 hours | $3.75 \times 10^4$ | 1.20 | $3.50 \times 10^5$ | 0.23 | $2.10 \times 10^5$ | 0.45 | $1.29 \times 10^5$ | 0.66 |
| A. niger 24 hours | $6.00 \times 10^5$ | −0.01 | $1.65 \times 10^4$ | 1.55 | $5.23 \times 10^4$ | 1.05 | $1.25 \times 10^4$ | 1.67 |
| A. niger 7 days | No Growth | 5.77 | No Growth | 5.77 | 83 | 3.85 | No Growth | 5.77 |
| A. niger 14 days | No Growth | 5.77 | No Growth | 5.77 | $6.60 \times 10^4$ | 0.95 | No Growth | 5.77 |
| A. niger 21 days | No Growth | 5.77 | No Growth | 5.77 | 4,000 | 2.17 | No Growth | 5.77 |
| A. niger 28 days | No Growth | 5.77 | No Growth | 5.77 | 5,400 | 2.04 | No Growth | 5.77 |

Materials: Materials such as facial tissue, paper and cotton towels, and sheets come in contact with microbes at every use. When the user is suffering from an infectious disease, the level of microbes contaminating surrounding materials escalates dramatically. Given that many microbes can survive for greater than 24 hours, the risk of exposure to others is high. Because the environment is more arid, microbes typically survive instead of proliferate waiting until an opportune host comes in contact and proliferation can begin again. Presence of compositions of the invention showed a greater than 99.999% reduction (5-log order reduction) in a microbial load using a modified preservative challenge test. See Table 5. The preservative efficacy test demonstrated the zinc treated sheet paper toweling and the cotton material both Passed the test for all five organisms tested against. The preservative efficacy test demonstrated the untreated sheet paper toweling and the cotton material both Failed the test for all five organisms tested against.

TABLE 5

| Organisms | 2 × 2 Sheet Paper Toweling Not Treated | | 2 × 2 Sheet Paper Toweling Zinc Treated | | 2 × 2 Cotton Material Square Not Treated | | 2 × 2 Cotton Material Square Zinc Treated | |
|---|---|---|---|---|---|---|---|---|
| | Average CFU | Log Reduction | Average CFU | Log Reduction | Average CFU | Log Reduction | Average CFU | Log Reduction |
| *E. coli* 0 hours | $2.02 \times 10^5$ | 0 | $2.02 \times 10^5$ | 0 | $2.02 \times 10^5$ | 0 | $2.02 \times 10^5$ | 0 |
| *E. coli* 8 hours | $1.05 \times 10^6$ | −0.72 | $1.40 \times 10^5$ | 0.16 | $1.65 \times 10^6$ | −0.91 | 1,258 | 2.21 |
| *E. coli* 24 hours | $4.80 \times 10^6$ | −1.38 | $2.85 \times 10^4$ | 0.85 | $1.95 \times 10^7$ | −1.98 | 180 | 3.05 |
| *E. coli* 7 days | $2.21 \times 10^6$ | −1.38 | 2,000 | 2.00 | $8.22 \times 10^6$ | −1.61 | No Growth | 5.31 |
| *E. coli* 14 days | $8.29 \times 10^6$ | −1.61 | 40 | 3.70 | $1.61 \times 10^7$ | −1.90 | No Growth | 5.31 |
| *E. coli* 21 days | $5.33 \times 10^6$ | −1.42 | No Growth | 5.31 | $6.40 \times 10^6$ | −1.50 | No Growth | 5.31 |
| *E. coli* 28 days | $7.22 \times 10^6$ | −1.55 | No Growth | 5.31 | $7.32 \times 10^6$ | −1.56 | No Growth | 5.31 |
| *S. aureus* 0 hours | $7.07 \times 10^5$ | 0 | $7.07 \times 10^5$ | 0 | $7.07 \times 10^5$ | 0 | $7.07 \times 10^5$ | 0 |
| *S. aureus* 8 hours | $9.00 \times 10^5$ | −0.10 | $2.30 \times 10^5$ | 0.49 | $3.75 \times 10^5$ | 0.28 | No Growth | 5.85 |
| *S. aureus* 24 hours | $1.67 \times 10^5$ | 0.63 | $9.38 \times 10^4$ | 0.88 | $1.23 \times 10^5$ | 0.76 | No Growth | 5.85 |
| *S. aureus* 7 days | $8.20 \times 10^4$ | 0.94 | 2,800 | 2.40 | $1.11 \times 10^5$ | 0.80 | No Growth | 5.85 |
| *S. aureus* 14 days | $1.50 \times 10^4$ | 1.67 | No Growth | 5.85 | $1.40 \times 10^4$ | 1.70 | No Growth | 5.85 |
| *S. aureus* 21 days | $1.30 \times 10^4$ | 1.74 | No Growth | 5.85 | TNTC | TNTC | No Growth | 5.85 |
| *S. aureus* 28 days | 2,000 | 2.55 | No Growth | 5.85 | $5.00 \times 10^4$ | 1.15 | No Growth | 5.85 |
| *P. aeruginosa* 0 hours | $2.02 \times 10^5$ | 0 | $2.02 \times 10^5$ | 0 | $2.02 \times 10^5$ | 0 | $2.02 \times 10^5$ | 0 |
| *P. aeruginosa* 8 hours | $1.25 \times 10^5$ | 0.21 | $8.65 \times 10^4$ | 0.37 | $1.86 \times 10^5$ | 0.04 | No Growth | 5.31 |
| *P. aeruginosa* 24 hours | $1.90 \times 10^6$ | −0.97 | $2.50 \times 10^5$ | −0.09 | $1.94 \times 10^7$ | −1.98 | No Growth | 5.31 |
| *P. aeruginosa* 7 days | $4.06 \times 10^6$ | −1.30 | 316 | 2.81 | $4.89 \times 10^6$ | −1.38 | No Growth | 5.31 |
| *P. aeruginosa* 14 days | $1.66 \times 10^7$ | −1.92 | No Growth | 5.31 | $1.81 \times 10^7$ | −1.95 | No Growth | 5.31 |
| *P. aeruginosa* 21 days | $2.09 \times 10^6$ | −1.02 | No Growth | 5.31 | $1.23 \times 10^6$ | −0.79 | No Growth | 5.31 |
| *P. aeruginosa* 28 days | $1.56 \times 10^7$ | −1.89 | No Growth | 5.31 | $3.07 \times 10^7$ | −2.18 | No Growth | 5.31 |
| *C. albicans* 0 hours | $1.92 \times 10^6$ | 0 | $1.92 \times 10^6$ | 0 | $1.92 \times 10^6$ | 0 | $1.92 \times 10^6$ | 0 |
| *C. albicans* 8 hours | $2.45 \times 10^6$ | −0.11 | $1.00 \times 10^6$ | 0.28 | $2.60 \times 10^6$ | −0.13 | $1.65 \times 10^6$ | 0.07 |
| *C. albicans* 24 hours | $1.30 \times 10^6$ | 0.17 | $1.10 \times 10^6$ | 0.24 | $1.65 \times 10^6$ | 0.07 | $1.35 \times 10^6$ | 0.15 |
| *C. albicans* 7 days | $3.69 \times 10^6$ | −0.28 | 4,700 | 2.61 | $5.20 \times 10^6$ | −0.43 | 9,000 | 2.33 |
| *C. albicans* 14 days | $2.24 \times 10^7$ | −1.07 | 250 | 3.89 | $1.46 \times 10^6$ | 0.12 | 900 | 3.33 |
| *C. albicans* 21 days | TNTC | TNTC | 11 | 5.24 | TNTC | TNTC | No Growth | 6.28 |
| *C. albicans* 28 days | TNTC | TNTC | No Growth | 6.28 | TNTC | TNTC | No Growth | 6.28 |
| *A. niger* 0 hours | $3.76 \times 10^5$ | 0 | $3.76 \times 10^5$ | 0 | $3.76 \times 10^5$ | 0 | $3.76 \times 10^5$ | 0 |
| *A. niger* 8 hours | $4.50 \times 10^5$ | −0.08 | $5.00 \times 10^5$ | −0.12 | $3.50 \times 10^5$ | 0.03 | $2.50 \times 10^5$ | 0.18 |

TABLE 5-continued

| Organisms | 2 × 2 Sheet Paper Toweling Not Treated | | 2 × 2 Sheet Paper Toweling Zinc Treated | | 2 × 2 Cotton Material Square Not Treated | | 2 × 2 Cotton Material Square Zinc Treated | |
|---|---|---|---|---|---|---|---|---|
| | Average CFU | Log Reduction | Average CFU | Log Reduction | Average CFU | Log Reduction | Average CFU | Log Reduction |
| *A. niger* 24 hours | $5.00 \times 10^5$ | −0.12 | $3.00 \times 10^5$ | 0.10 | $1.50 \times 10^5$ | 0.40 | $3.00 \times 10^5$ | 0.10 |
| *A. niger* 7 days | $2.50 \times 10^4$ | 1.18 | $4.40 \times 10^4$ | 0.93 | $4.89 \times 10^6$ | −1.11 | $1.20 \times 10^4$ | 1.50 |
| *A. niger* 14 days | $7.02 \times 10^6$ | −1.27 | $4.10 \times 10^4$ | 0.96 | $3.02 \times 10^7$ | −1.91 | 5,000 | 1.88 |
| *A. niger* 21 days | 1,360 | 2.44 | 2,120 | 2.25 | $1.00 \times 10^5$ | 0.58 | 420 | 2.95 |
| *A. niger* 28 days | 1,000 | 2.58 | 8,700 | 1.64 | $8.00 \times 10^4$ | 0.67 | 55 | 3.84 |

*TNTC means Too Numerous To Count

What is claimed is:

1. A method of reducing microbial growth comprising:
   introducing an antimicrobial composition in foods or beverages susceptible to attack by at least one microorganism selected from the group consisting of *Escherichia coli, Pseudomonas aeruginosa, Candida albicans* and *Aspergillus niger;*
   wherein the antimicrobial composition consists of a first zinc compound, a second zinc compound, a third compound, and silicone;
   wherein the antimicrobial composition consists of between about 0.10 wt % and 25 wt % of the first zinc compound selected from the group consisting of zinc butyrate, zinc glycerate, zinc glycolate, zinc formate, zinc phthalocyanine, zinc picolinate, and zinc tartrate;
   wherein the antimicrobial composition consists of between about 0.01 wt % and 10 wt % of the second zinc compound selected from the group consisting of zinc acetate, zinc butyrate, zinc chloride, zinc citrate, zinc gluconate, zinc glycerate, zinc glycolate, zinc formate, zinc lactate, zinc phthalocyanine, zinc picolinate, zinc proprionate, zinc salicylate, zinc tartrate, zinc undecylenate, colloidal zinc, zinc ligands, and zinc alloys; and
   wherein the antimicrobial composition consists of between about 0.05 wt % and 10 wt % of the third compound, wherein the third compound consists of mandelic acid.

2. The method of claim 1, wherein the step of introducing said antimicrobial composition is by spraying, soaking, fogging, or impregnation.

3. The method of claim 1, wherein the introducing comprises introducing the composition to food on a food transport line.

4. The method of claim 1, wherein the introducing comprises introducing the composition to food via a dip pan.

5. The method of claim 1, wherein the introducing comprises introducing the composition to food via an air circulation system.

6. The method of claim 1, wherein the introducing comprises introducing the composition to food via aseptic packaging.

* * * * *